US011771421B2

(12) United States Patent
Smith et al.

(10) Patent No.: US 11,771,421 B2
(45) Date of Patent: Oct. 3, 2023

(54) SYSTEMS, DEVICES, AND RELATED METHODS FOR FASTENING TISSUE (71) Applicant: Boston Scientific Scimed, Inc., Maple Grove, MN (US)

(72) Inventors: Paul Smith, Smithfield, RI (US); Gary Jordan, Litchfield, NH (US); Nathan Cummings, Worcester, MA (US); Ryan Wales, Northborough, MA (US); Douglas Melanson, Natick, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 247 days.

(21) Appl. No.: 16/924,609

(22) Filed: Jul. 9, 2020

(65) Prior Publication Data
US 2021/0007736 A1 Jan. 14, 2021

Related U.S. Application Data (60) Provisional application No. 62/872,481, filed on Jul. 10, 2019.

(51) Int. Cl.
*A61B 17/068* (2006.01)
*A61B 17/00* (2006.01)
*A61B 17/072* (2006.01)

(52) U.S. Cl.
CPC .... *A61B 17/0686* (2013.01); *A61B 17/00234* (2013.01); *A61B 17/07207* (2013.01);
(Continued)

(58) Field of Classification Search
CPC ............. A61B 1/012; A61B 17/00234; A61B 17/0686; A61B 17/07207;
(Continued)

(56) References Cited

U.S. PATENT DOCUMENTS 5,254,126 A * 10/1993 Filipi ................. A61B 17/0469
606/139
5,297,536 A * 3/1994 Wilk ................. A61B 17/00234
606/140

(Continued)

FOREIGN PATENT DOCUMENTS

EP 0630614 B1 8/1997
EP 2687164 A2 1/2014

*Primary Examiner* — Robert F Long
*Assistant Examiner* — Eduardo R Ferrero
(74) *Attorney, Agent, or Firm* — Bookoff McAndrews, PLLC (57) ABSTRACT An endoscopic tissue fastening device may include a body having a first portion and a second portion arranged alongside the first portion. The second portion may extend distally of the first portion and may terminate in a distal end face of the body. The device may further include a tissue fastening assembly having a fastening head with a proximal end and a distal end. The fastening head may be deflectable at a location between the proximal end and the distal end of the fastening head. The tissue fastening assembly may be received within a lumen of the body. Further, the body may be moveable between an unarticulated configuration and an articulated configuration. In the articulated configuration, a central longitudinal axis of the second portion of the body may be substantially parallel with a central longitudinal axis of the tissue fastening assembly.

12 Claims, 6 Drawing Sheets

(52) U.S. Cl.
CPC ............... *A61B 2017/00296* (2013.01); *A61B 2017/07271* (2013.01)

(58) Field of Classification Search
CPC  A61B 2017/00296; A61B 2017/00309; A61B 2017/0034; A61B 2017/07271; A61B 2017/2905; A61B 2017/2927; A61B 2017/00314; A61B 2017/305
See application file for complete search history.

(56) References Cited

U.S. PATENT DOCUMENTS

| | | | | |
|---|---|---|---|---|
| 5,403,326 | A * | 4/1995 | Harrison | A61B 17/10 227/181.1 |
| 5,571,116 | A * | 11/1996 | Bolanos | A61B 17/07207 606/151 |
| 5,573,543 | A | 11/1996 | Akopov et al. | |
| 5,607,094 | A * | 3/1997 | Clark | A61B 17/072 227/176.1 |
| 5,797,931 | A * | 8/1998 | Bito | A61B 17/1285 606/127 |
| 5,868,760 | A * | 2/1999 | McGuckin, Jr. | A61B 17/07207 606/139 |
| 6,119,913 | A | 9/2000 | Adams et al. | |
| 6,159,146 | A * | 12/2000 | El Gazayerli | A61B 17/1285 600/106 |
| 6,179,195 | B1 * | 1/2001 | Adams | A61B 17/07207 606/139 |
| 6,398,795 | B1 * | 6/2002 | McAlister | A61B 17/072 606/139 |
| 7,841,503 | B2 | 11/2010 | Sonnenschein et al. | |
| 8,961,396 | B2 * | 2/2015 | Azarbarzin | A61B 17/320016 600/106 |
| 8,968,337 | B2 * | 3/2015 | Whitfield | A61B 17/1285 606/143 |
| 2002/0047036 | A1 * | 4/2002 | Sullivan | A61B 17/07207 227/19 |
| 2002/0078967 | A1 * | 6/2002 | Sixto, Jr. | A61B 90/50 128/898 |
| 2002/0082621 | A1 * | 6/2002 | Schurr | A61B 17/0643 606/151 |
| 2003/0132267 | A1 * | 7/2003 | Adams | A61B 17/07207 227/176.1 |
| 2004/0006351 | A1 * | 1/2004 | Gannoe | A61B 17/30 606/139 |
| 2004/0082963 | A1 * | 4/2004 | Gannoe | A61F 5/0076 606/153 |
| 2004/0138529 | A1 * | 7/2004 | Wiltshire | A61B 1/0055 600/144 |
| 2004/0138682 | A1 * | 7/2004 | Onuki | A61B 17/0643 606/205 |
| 2004/0162568 | A1 * | 8/2004 | Saadat | A61B 1/2736 606/139 |
| 2004/0167546 | A1 * | 8/2004 | Saadat | A61B 17/00234 606/144 |
| 2004/0181242 | A1 * | 9/2004 | Stack | A61B 17/00234 606/139 |
| 2004/0193190 | A1 * | 9/2004 | Liddicoat | A61B 17/072 606/153 |
| 2005/0080438 | A1 * | 4/2005 | Weller | A61B 17/29 606/153 |
| 2005/0177176 | A1 * | 8/2005 | Gerbi | A61B 17/07207 606/139 |
| 2005/0203547 | A1 * | 9/2005 | Weller | A61B 17/072 606/139 |
| 2005/0256533 | A1 * | 11/2005 | Roth | A61B 17/29 606/167 |
| 2006/0106288 | A1 * | 5/2006 | Roth | A61B 17/072 604/206 |
| 2006/0151568 | A1 * | 7/2006 | Weller | A61B 17/07207 227/175.1 |
| 2007/0167960 | A1 * | 7/2007 | Roth | A61B 17/07207 606/153 |
| 2007/0187453 | A1 * | 8/2007 | Smith | A61B 17/068 227/175.1 |
| 2009/0069806 | A1 * | 3/2009 | De La Mora Levy | A61B 17/072 606/198 |
| 2010/0116867 | A1 * | 5/2010 | Balbierz | A61B 17/068 227/175.1 |
| 2010/0320252 | A1 * | 12/2010 | Viola | A61B 17/068 227/176.1 |
| 2011/0163146 | A1 | 7/2011 | Ortiz et al. | |
| 2012/0143218 | A1 * | 6/2012 | Beardsley | A61B 17/00234 606/142 |
| 2012/0193396 | A1 * | 8/2012 | Zemlok | A61B 17/07207 227/176.1 |
| 2012/0228358 | A1 * | 9/2012 | Zemlok | A61B 17/07207 227/176.1 |
| 2012/0248167 | A1 * | 10/2012 | Flanagan | A61B 17/07207 227/2 |
| 2012/0255986 | A1 * | 10/2012 | Petty | A61F 5/0086 227/176.1 |
| 2013/0092719 | A1 * | 4/2013 | Kostrzewski | A61B 17/105 227/177.1 |
| 2013/0098966 | A1 * | 4/2013 | Kostrzewski | A61B 17/07207 606/1 |
| 2014/0131421 | A1 * | 5/2014 | Viola | A61B 17/068 227/175.1 |
| 2014/0148828 | A1 | 5/2014 | Ewers et al. | |
| 2014/0239040 | A1 * | 8/2014 | Fanelli | A61B 17/07207 227/175.2 |
| 2014/0291383 | A1 * | 10/2014 | Spivey | A61B 17/320016 227/177.1 |
| 2015/0001274 | A1 * | 1/2015 | Cole | A61B 17/072 227/176.1 |
| 2015/0164502 | A1 * | 6/2015 | Richard | A61B 17/00234 74/665 M |
| 2015/0173755 | A1 * | 6/2015 | Baxter, III | A61B 17/072 227/180.1 |
| 2015/0230793 | A1 * | 8/2015 | Kostrzewski | A61B 17/0644 227/176.1 |
| 2015/0297199 | A1 * | 10/2015 | Nicholas | A61B 17/29 606/1 |
| 2015/0374364 | A1 * | 12/2015 | Gettinger | A61B 17/07292 227/175.1 |
| 2016/0106425 | A1 * | 4/2016 | Yates | H02J 7/0044 320/113 |
| 2016/0174977 | A1 * | 6/2016 | Lytle, IV | A61B 17/07207 227/180.1 |
| 2017/0095251 | A1 * | 4/2017 | Thompson | A61B 17/3468 |
| 2017/0135695 | A1 * | 5/2017 | Shelton, IV | A61B 34/35 |
| 2018/0021051 | A1 * | 1/2018 | Worrell | A61B 17/2812 227/175.1 |
| 2018/0092635 | A1 | 4/2018 | Csiky | |
| 2018/0289372 | A1 * | 10/2018 | Nie | A61B 17/295 |
| 2019/0069895 | A1 * | 3/2019 | Satti, III | A61B 17/320016 |

* cited by examiner

SYSTEMS, DEVICES, AND RELATED METHODS FOR FASTENING TISSUE

CROSS-REFERENCE TO RELATED APPLICATION(S)

This application claims the benefit of priority from U.S. Provisional Application No. 62/872,481, filed on Jul. 10, 2019, which is incorporated by reference herein in its entirety.

TECHNICAL FIELD

Various aspects of the present disclosure relate generally to tissue fastening. More specifically, at least certain embodiments of the present disclosure relate to systems, devices, and related methods for manipulating an endoscopic tissue fastening device and fastening tissue, among other aspects.

BACKGROUND

Tissue fastening (e.g., stapling) is used in many laparoscopic procedures. These procedures often involve resecting portions or sections of tissue, followed by closing using staples. An example of a common procedure would be colorectal anastomosis. In hybrid surgeries where physicians use laparoscopic and endoscopic platforms to conduct a procedure, a rigid stapler is often used. Linear staplers include long rigid members which are incapable of being navigated through tortuous anatomy without causing trauma to the tissue. Physicians also are moving towards endoscopic, outpatient procedures, which would require endoscopic stapling.

It is with the above considerations in mind that the improvements of the present disclosure may be useful.

SUMMARY

Aspects of the present disclosure relate to, among other things, systems, devices, and methods for fastening tissue, e.g., a flexible endoscope platform with stapling capability. Each of the aspects disclosed herein may include one or more of the features described in connection with any of the other disclosed aspects.

In one example, an endoscopic tissue fastening device may include a body having a first portion and a second portion arranged alongside the first portion. The second portion may extend distally of the first portion and may terminate in a distal end face of the body. The device may further include a tissue fastening assembly having a fastening head with a proximal end and a distal end. The fastening head may be deflectable at a location between the proximal end and the distal end of the fastening head. The tissue fastening assembly may be received within a lumen of the body. Further, the body may be moveable between an unarticulated configuration and an articulated configuration. In the articulated configuration, a central longitudinal axis of the second portion of the body may be substantially parallel with a central longitudinal axis of the tissue fastening assembly.

Examples of the endoscopic tissue fastening device may include any one or more of the following features. The lumen may terminate proximally of the distal end face. A cross-sectional shape of the first portion may be circular, and a cross-sectional shape of the second portion may be D-shaped. The tissue fastening assembly may include a flexible configuration and a stabilized configuration. In the articulated configuration of the body, the tissue fastening assembly may be arranged in the flexible configuration. In the stabilized configuration, the fastening head of the tissue fastening assembly may extend distally of the distal end face of body. In the stabilized configuration, the fastening head of the tissue fastening assembly may be articulatable along an articulation joint proximal of the fastening head such that the central longitudinal axis of the tissue fastening assembly may be movable towards or away from the central longitudinal axis of the second portion of the body. The tissue fastening assembly may include a staple cartridge, and in the flexible configuration, at least a portion of the staple cartridge distal of the location may be deflected relative to another portion of the staple cartridge proximal of the location. The staple cartridge may include at least one flexible joint between a proximal end of the staple cartridge and a distal end of the staple cartridge. A support may be positioned along the second portion of the body, and in the articulated configuration, a distal end of the tissue fastening assembly may be received within the support. At least a portion of the tissue fastening assembly may be axially moveable relative to the support. In the stabilized configuration, a flexible connection of the tissue fastening assembly may be received within the support and may be prevented from flexing by the support. The tissue fastening assembly may include a sheath coupled to an articulation joint via a flexible connection, the flexible connection may include at least one notch therein, and the tissue fastening assembly may include a staple cartridge distal of the articulation joint. A stabilizer may be moveably coupled to a staple cartridge of the tissue fastening assembly, in a first position, the stabilizer may permit bending of the staple cartridge along a joint of the staple cartridge, and in a stabilized configuration, the stabilizer may span the joint of the staple cartridge so as to prevent bending of the staple cartridge along the joint.

In a further example, a method of endoscopic tissue fastening may include articulating an endoscopic tissue fastening device having a lumen with a tissue fastening assembly at least partially received within the lumen; and transitioning the tissue fastening assembly from a flexible configuration to a stabilized configuration, wherein in the flexible configuration, a first portion of a tissue fastening cartridge is moveable relative to a second portion of the tissue fastening cartridge, and wherein in the stabilized configuration, the first portion of the tissue fastening cartridge is prevented from moving relative to the second portion of the tissue fastening cartridge. Additionally, the method may include ejecting one or more tissue fasteners from the tissue fastening cartridge to fasten tissue.

Examples of the method may include any one or more of the following features. The method may include, during the articulating the endoscopic tissue fastening device, the tissue fastening assembly may be arranged in the flexible configuration at a distal end of the tissue fastening device. The method may further include, in the stabilized configuration, articulating the tissue fastening cartridge relative to the endoscopic tissue fastening device.

In a further example, an endoscopic tissue fastening device may include a body extending between a proximal end and a distal end and including at least one lumen. Additionally, an endoscopic tissue fastening device may include a tissue fastening assembly positioned within the at least one lumen of the body and the tissue fastening assembly may include a sheath coupled to a tissue fastening head via a flexible connection, an articulation joint located at a proximal end of the tissue fastening head, and a flexible joint positioned between a proximal end and a distal end of a fastener cartridge of the tissue fastening head.

Examples of the endoscopic tissue fastening device may include any one or more of the following features. The flexible joint may be positioned between the proximal end and the distal end of the fastener cartridge and may include at least one notch or cutout along the fastener cartridge. The body may include a first portion with a first cross-sectional shape and a second portion with a second cross-sectional shape different than the first cross-sectional shape, and the second portion may be distal of the first portion and extends to a distal end face of the body. The at least one lumen may terminate proximally of the distal end face of the body, the cross-sectional shape of the first portion may be circular, and the cross-sectional shape of the second portion may be D-shaped.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn to systems, devices, and methods for coupling, cutting, and resecting tissue, among other aspects. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject. The term "tissue fastening" may refer, for example, to stapling, fixing, attaching, fastening, or otherwise joining two portions of tissue together. The term "fastener" may include staples, clips, elastic bands, suture, or any other fastener known in the art.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of the stated value unless otherwise stated.

Figure 1:
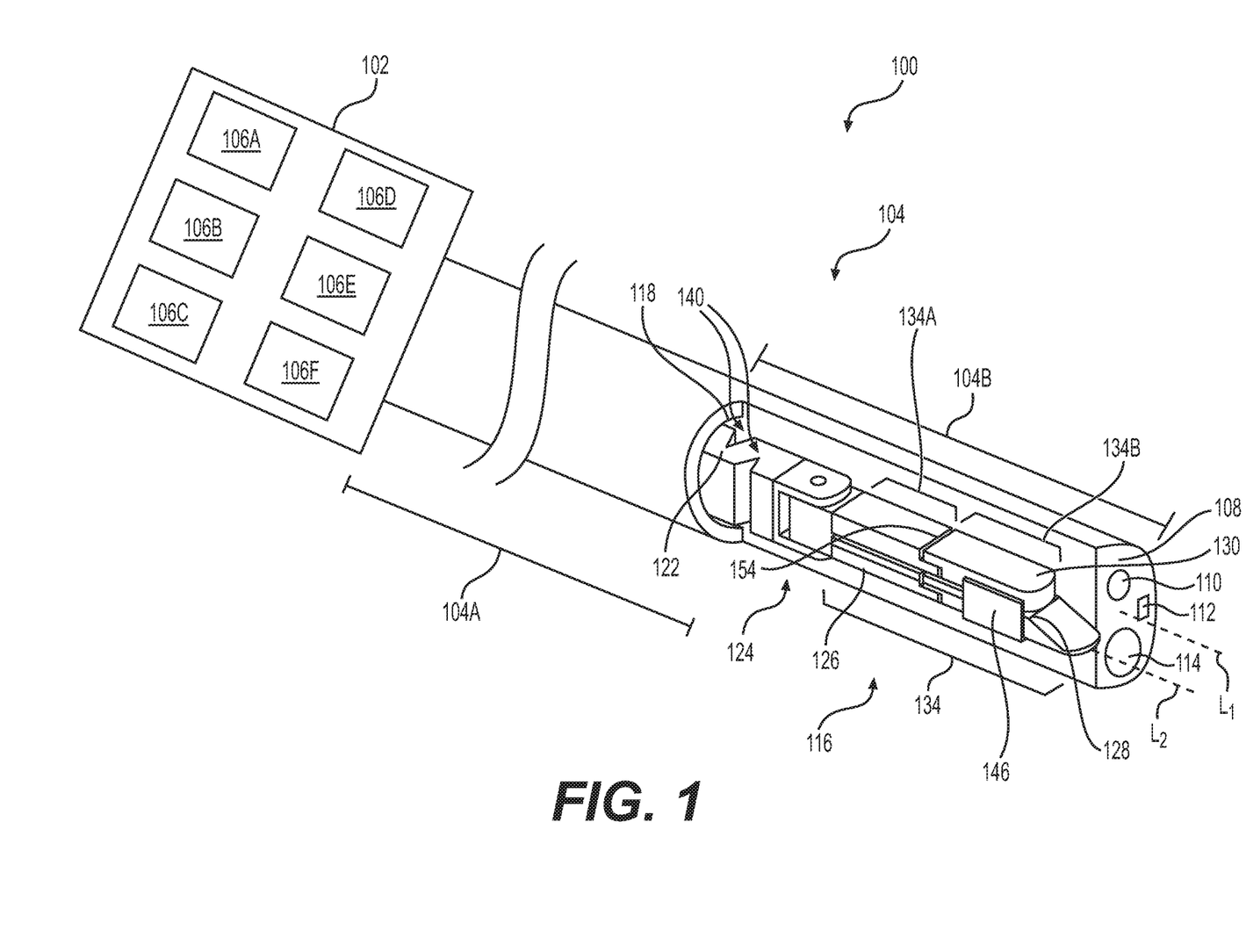
FIG. 1 is a perspective view of an exemplary endoscopic tissue fastening device, according to aspects of this disclosure.

FIG. 1 illustrates an endoscopic tissue fastening device 100 which may be a surgical stapling apparatus configured to engage body tissue, apply a plurality of surgical fasteners thereto, and form an incision in the fastened body tissue during minimally invasive surgical procedures, such as endoscopic procedures. Endoscopic tissue fastening device 100 may be used to apply surgical clips or other fasteners, but will be primarily discussed in the context of applying staples from a staple cartridge.

As shown, endoscopic tissue fastening device 100 extends between a proximal end and a distal end. At the proximal end is a handle 102 coupled to a longitudinally extending body 104. Handle 102 may include one or more actuators 106A-106F for actuating various features of endoscopic tissue fastening device 100, as will be described in further detail below. Although device 100 may be a dedicated endoscope for flexible stapling, reference to endoscopes or endoscopy should not be construed as limiting the possible applications of the disclosed aspects. For example, the disclosed aspects may be used with duodenoscopes, bronchoscopes, ureteroscopes, colonoscopes, catheters, diagnostic or therapeutic tools or devices, or other types of medical devices. While FIG. 1 illustrates six distinct actuators, the disclosure is not so limited. Rather, more or fewer actuators may be provided without departing from the scope of this application. For example, one or more of actuators 106A-106F may be actuated to initiate multiple features of endoscopic tissue fastening device 100. In other words, a single actuator could be used to move an anvil 130 both away from and toward a staple cartridge 128 (or vice versa) during a stapling or tissue fastening procedure, as will be described in further detail below. Additionally, while handle 102 and actuators 106A-106F are illustrated schematically, such features may have any appropriate shape, configuration, and/or orientation without departing from the scope of the present disclosure. For example, handle 102 may be ergonomically shaped to promote secure grip by a user, while actuators 106A-106F may be any one or more of buttons, dials, rockers, sliders, etc., configured to move, deflect, bend, rotate, pivot, or otherwise be adjusted relative to handle 102 and/or body 104 to actuate various features of endoscopic tissue fastening device 100, as will be described in further detail below. Additionally, it is understood that each of actuators 106A-106F may initiate/actuate features of endoscopic tissue fastening device 100 via an activation wire (or the like). In other words, actuation of each actuator 106A-106F may result in actuation of an activation wire (not shown) having a proximal end operatively engaged with the respective actuator 106A-106F and a distal end operatively engaged with the respective feature of endoscopic tissue fastening device 100. In such a manner, an activating force may be transmitted from a user at handle 102 along body 104, so as to actuate features of endoscopic tissue fastening device 100.

As noted above, the proximal end of body 104 may be coupled to handle 102 while a distal end of body 104 may terminate in a distal end face 108. In some arrangements, distal end face 108 may be a distal end face of a cap coupled (either removably or permanently) to the distal end of body 104.

Endoscopic tissue fastening device 100 may include one or more of an illumination device 110, an optics device 112, one or more lumens 114, and a tissue fastening assembly 116. For example, illumination device 110 may include one or more of a fiber optic device (e.g., a light cable) or a light-emitting diode (LED) so as to provide illumination light to a location within a body of a subject distal of distal end face 108. Optics device 112 may include any appropriate device configured to provide a visual image of an internal location of the body of the subject. For example, optics device 112 may include one or more optical elements (e.g., lens, cameras, etc.). The one or more lumens 114 of body 104 may be arranged at any appropriate location about distal end face 108 and extend proximally to handle 102. In some arrangements, the one or more lumens 114 may be arranged to provide irrigation and/or aspiration fluid and/or may be arranged to deliver one or more medical devices (e.g., a tissue acquisition tool, forceps, graspers, etc.) In such cases, the one or more lumens 114 may be fluidly coupled to one or more ports (not shown) of handle 102. Such ports may be, in turn, fluidly coupled to one or more sources of irrigation and/or aspiration fluid for delivery via the one or more lumens 114, and/or arranged for insertion of the one or more medical devices therethrough for delivery via the one or more lumens 114. Further, the one or more lumens 114 may be arranged to receive one or more articulation wires (not shown) or the like for imparting selective articulation to at least the distal end of body 104. Additionally, one or more of actuators 106A-106F may be arranged to actuate delivery of irrigation/aspiration fluid, extension/retraction or activation of the medical device, activation of illumination device 110, activation of optics device 112, and/or activation/manipulation of one or more articulation wires to impart articulation of body 104. For example, actuator 106A may be operably connected to one or more articulation wires such that manipulation of actuator 106A results in articulation of body 104.

As shown in FIG. 1, body 104 may include a first portion 104A and a second portion 104B. For example, first portion 104 may encompass a majority of body 104, and include the proximal end of body 104. Second portion 1046 may encompass a remainder of body 104, including the distal end and distal end face 108 of body 104. As shown, body 104 may have a varied exterior cross-sectional shape and/or size. For example, first portion 104A may have a first exterior cross-sectional shape (e.g., circular) or size, while second portion 1046 may have a second exterior cross-sectional shape (e.g., D-shaped) or size. In some arrangements, for example, a lumen 118, in which tissue fastening assembly 116 is arranged, may extend along first portion 104A of body 104 and terminate proximally of second portion 104B. Said differently, lumen 118 may extend along only first portion 104A, and therefore, second portion 1046 may be reduced and/or adjusted in shape or size, respectively, due to the absence of lumen 118. In such a manner, body 104 may define a "pocket" within which tissue fastening assembly 116 may be arranged. In other words, tissue fastening assembly 116 may be positioned alongside body 104. For example, a central longitudinal axis L1 of second portion 104B may be arranged substantially parallel to a central longitudinal axis L2 of tissue fastening assembly 116. Additionally, as shown in FIG. 1, a support 146 may be fixedly arranged along a portion of second portion 104B. That is, support 146 may be secured (so as to not be moveable) relative to second portion 104B in any appropriate manner (e.g., fasteners, adhesives, etc.). Support 146 may selectively receive at least a portion of tissue fastening assembly 116 therein to maintain an alignment of tissue fastening assembly 116 relative to body 104, as will be discussed in further detail below. Support 146 may have any appropriate shape configured to support tissue fastening assembly 116. For example, support 146 may be U-shaped, L-shaped, or C-shaped.

Figure 2A:
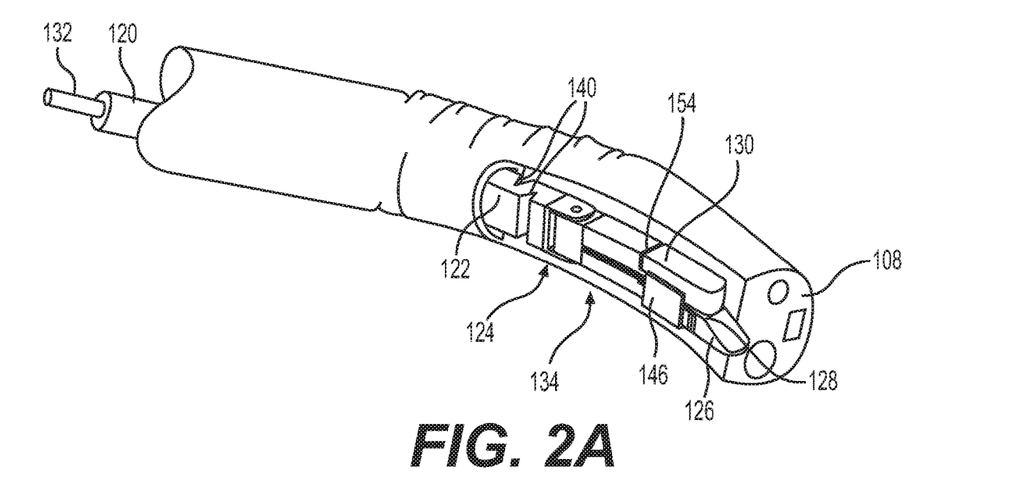
FIGS. 2A-2E illustrate a distal end of the endoscopic tissue fastening device of FIG. 1 during delivery, extension, articulation, opening, and stapling of tissue, respectively, according to aspects of this disclosure.
Figure 2B:
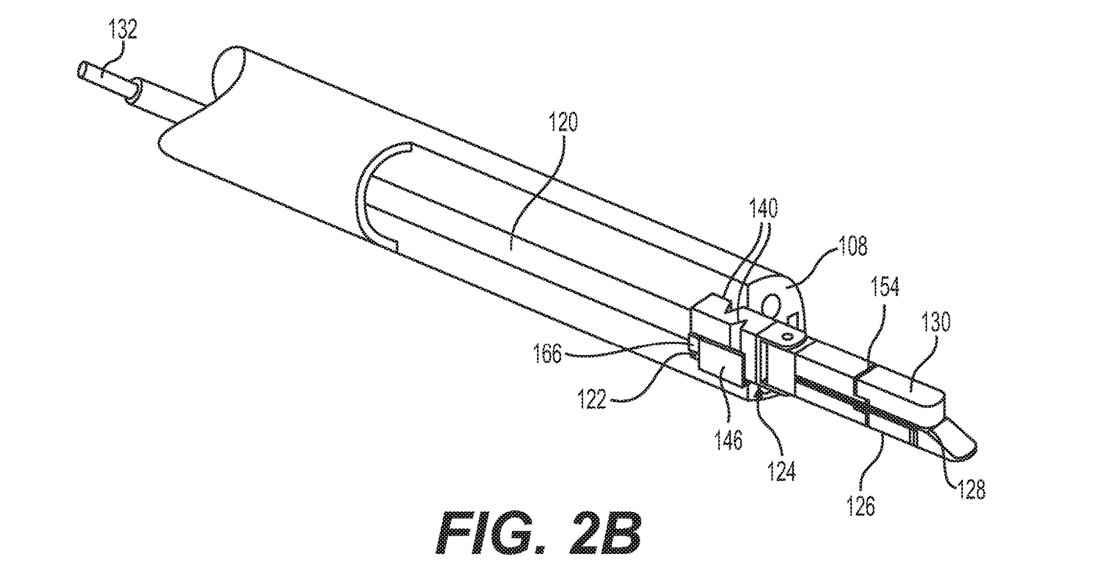
Figure 2C:
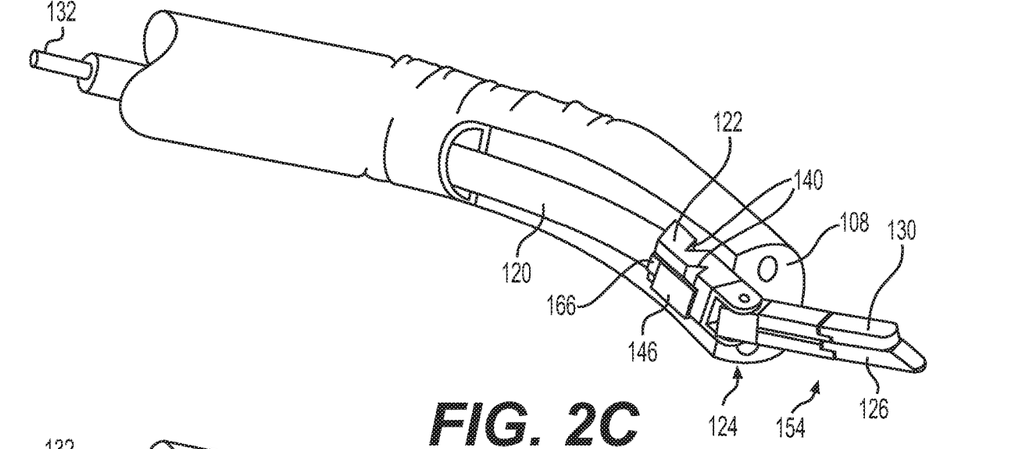
Figure 2D:
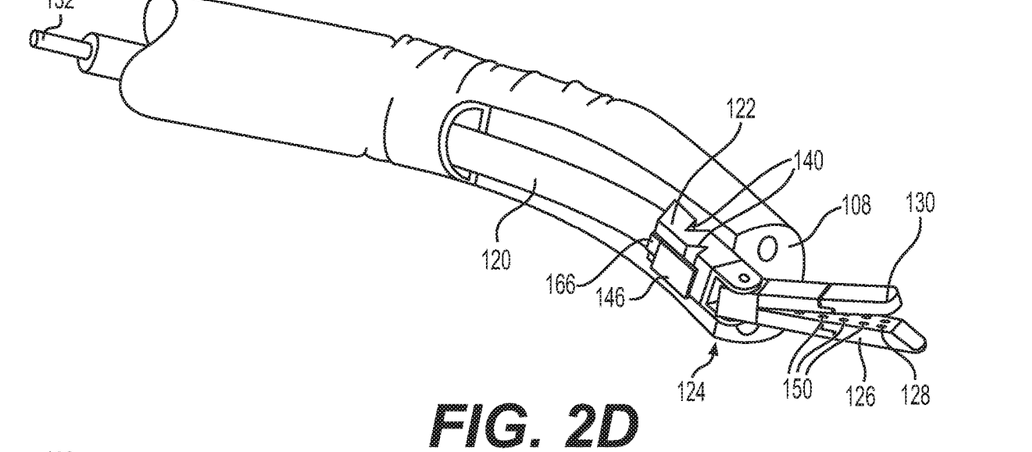
Figure 2E:
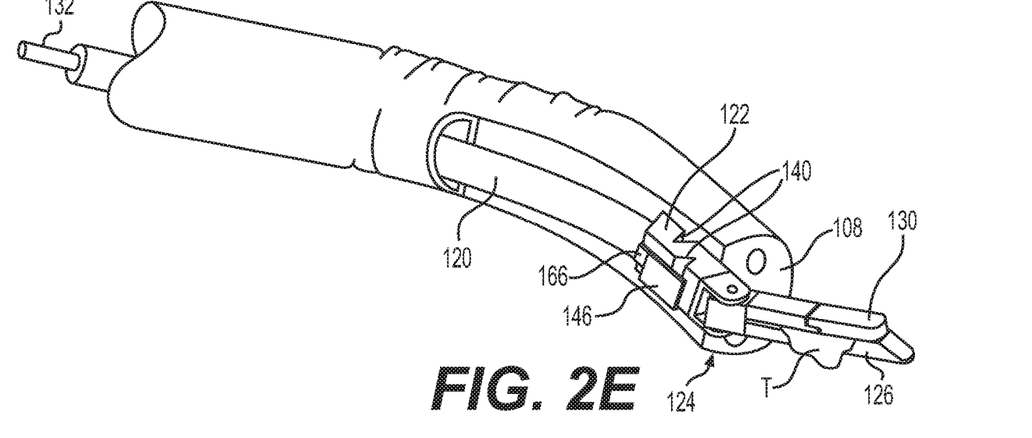

Tissue fastening assembly 116 may include a sheath 120 (FIG. 2A-2E), a flexible connection 122, an articulation joint 124, a fastening head 134 (including a cartridge housing 126, a cartridge 128, and an anvil 130), and an actuation line 132 (FIG. 2A-2E). As discussed in further detail below, tissue fastening assembly 116 may include a first unrestrained, bendable, or otherwise flexible configuration as shown in FIGS. 1 and 2A, a second restrained, stiffened, or otherwise stabilized configuration as shown in FIG. 2B, an optional third articulated or deflected configuration as shown in FIG. 2C, an open configuration as shown in FIG. 2D, and a fastening configuration as shown in FIG. 2E.

As will be described in further detail below, manipulation of actuation line 132 may facilitate transitioning tissue fastening assembly 116 between the first configuration and the second configuration. Actuation line 132 may be any appropriate longitudinally extending member configured to impart an axial force on one or both of the fastening head 134 and sheath 120. For example, actuation line 132 may be a rod, wire, tube, hypotube, etc. A proximal end of actuation line 132 may be coupled to one of actuators 106A-106F of handle 102. In such a manner, a user may actuate actuation line 132 via manipulation of the one of actuators 106A-106F. For example, actuation line 132 may be operatively coupled to actuator 106B, and actuation of actuator 106B may result in axial advancement or retraction of actuation line 132, thereby resulting in axial advancement or retraction of one or both sheath 120 and fastening head 134 relative to body 104, as will be described in further detail below.

Sheath 120 may terminate in (or be coupled to) flexible connection 122. Flexible connection 122 may facilitate flexing/bending of tissue fastening assembly 116. For example, flexible connection 122 may permit bending or deflecting of fastening head 134 relative to sheath 120. Indeed, flexible connection 122 may be made of any appropriate material, e.g., a polymeric and/or a metallic material, and may be configured to permit or promote bending. That is, flexible connection 122 may have one or more portions of reduced thickness, cut-outs, grooves, notches, or the like arranged to permit bending. For example, as shown in FIG. 1, flexible connection 122 may include one or more notches 140. Notches 140 may be generally v-shaped, as shown in FIG. 1, although the disclosure is not so limited. Indeed, notches 140 may have any appropriate shape configured to permit or promote bending. Additionally, while two notches 140 longitudinally spaced apart and arranged on opposing sides of flexible connection 122 are shown (see, e.g., FIG. 2A), any number, arrangement, orientation, or size may be used without departing from the scope of the present disclosure.

Flexible connection 122 may terminate in (or be coupled to) articulation joint 124. Articulation joint 124 may include any appropriate mechanical connection configured to permit movement of fastening head 134 relative to body 104 (see, e.g., FIGS. 2A, and 2C-2E). For example, articulation joint 124 may comprise a pivot, hinge, and/or ball and socket connection. Articulation joint 124 may be operatively coupled (e.g., via a wire or the like) to one of actuators 106A-106F, e.g., 106C. Accordingly, manipulation of actuator 106C may result in articulation of fastening head 134 relative to body 104. Alternatively, fastening head 134 may be operatively coupled (e.g., via a wire or the like) to actuator 106C such that manipulation of actuator 106C may result in articulation of fastening head 134 relative to body 104 via articulation joint 124. Indeed, upon actuation of actuator 106C, fastening head 134 may move toward or away from body 104. For example, fastening head 134 may move (e.g., articulate at an articulation location) toward the central longitudinal axis L1 of second portion 104b so as to be arranged in front of distal end face 108, and/or may be moved away from central longitudinal axis L1 of second portion 104b to so as to extend away from distal end face 108.

As noted above, fastening head 134 collectively includes cartridge housing 126, cartridge 128, and anvil 130, and may be coupled to articulation joint 124. Cartridge housing 126 may be arranged so as to receive cartridge 128 therein. Cartridge 128 may be removable from cartridge housing 126 (e.g., cartridge housing 126 may be reloaded with a new cartridge, if needed). In some examples, however, cartridge 128 may be integrally formed in cartridge housing 126, and therefore, non-removable. Anvil 130 may be rotatably or pivotably coupled to cartridge housing 126. In some examples, anvil 130 may be rotatably biased toward the open configuration (FIG. 2D), e.g., biased away from cartridge housing 126 and cartridge 128, thereby creating a space between the anvil 130 and cartridge housing 126/cartridge 128. Alternatively, anvil 130 may be rotatably biased toward the fastening configuration (FIG. 2E), e.g., biased toward the cartridge housing 126 and cartridge 128. In either arrangement, anvil 130 may be moved toward or away from cartridge housing 126 and cartridge 128 via actuation of one of actuators 106A-106F, e.g., 106D. That is, upon actuation/manipulation of actuator 106D, anvil 130 may move toward the open configuration and/or move toward the fastening configuration. That is, anvil 130 may be rotated/pivoted about an axis so as to contact cartridge housing 126/cartridge 128 to pinch tissue T (FIG. 2E) between anvil 130 and cartridge housing 126/cartridge 128, so as to provide a surface for which staples may be driven into when ejected from cartridge 128.

Cartridge 128 may contain a plurality of surgical fasteners, such as staples, and the fasteners may be deployed from cartridge 128 when under the influence of a driving force exerted by an actuation sled (not shown). A plurality of spaced apart longitudinal slots 150 (FIGS. 2D, 3, 5A, 5B) in cartridge 128 may permit staples to pass through cartridge 128 and pierce tissue, as will be described in further detail below. In some examples, the actuation sled may be arranged to move proximally in a longitudinal direction from a distal end of cartridge 128 toward a proximal end of cartridge 128 when actuated, contacting fasteners within cartridge 128 and pushing the fasteners through longitudinal slots 150 in order to couple fasteners to tissue. Alternatively, in some examples, the actuation sled may be arranged to move distally in a longitudinal direction from a proximal end of cartridge 128 toward a distal end of cartridge 128 when actuated. In either manner, actuation sled may be actuated via one of actuators 106A-106F, e.g., 106E (via a wire or the like operatively connected to actuator 106E). For example, actuation, actuation or manipulation of actuator 106E may eject or deploy fasteners into tissue. In some examples, a single fastener may extend through each slot 150. Each fastener may be partially within slot 150 prior to deployment to assist with alignment of the fastener with the slot 150. In some examples, two (or more) actuation sleds (not shown) may be required to actuate two (or more) different longitudinal rows of fasteners in cartridge 128.

Figure 3:
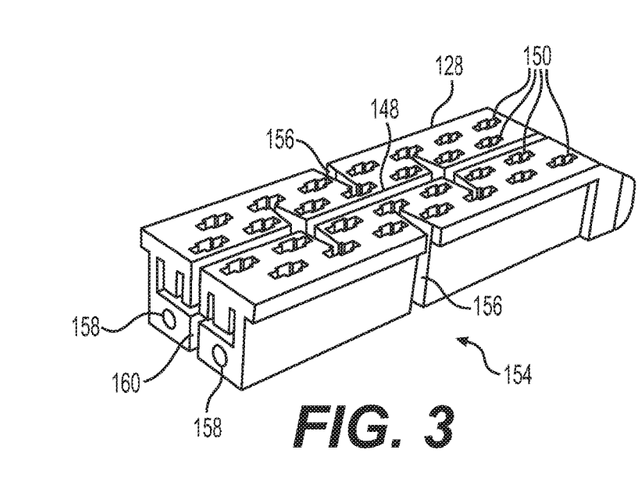
FIG. 3 is a perspective view of a staple cartridge, according to aspects of this disclosure.
Figure 5A:
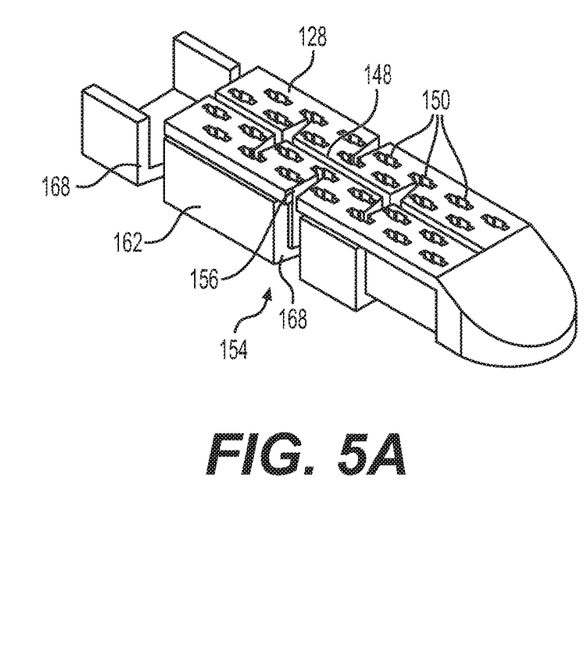
FIG. 5A is a perspective view of the stabilizer of FIG. 4 in a first position relative to the staple cartridge, according to aspects of the present disclosure.
Figure 5B:
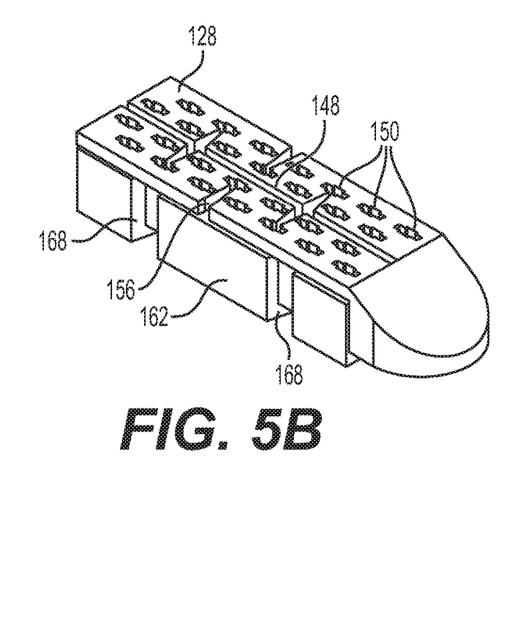
FIG. 5B is a perspective view of the stabilizer of FIG. 4 in a second position relative to the staple cartridge, according to aspects of the present disclosure.

Cartridge 128 may also include an elongate longitudinal slot 148 (FIGS. 3, 5A, 5B). The elongate longitudinal slot 148 may be configured to receive and/or support a resecting tool, such as a knife blade (not shown). The elongate longitudinal slot 148 may be positioned on a side of cartridge 128 and may run longitudinally from the proximal end to the distal end of cartridge 128. Anvil 130 may include a groove (not shown) positioned longitudinally that may align with elongated longitudinal slot 148 when anvil 130 is in the fastening configuration (FIG. 2E) and such groove may be configured to receive the resecting tool. The resecting tool may be operably coupled to one of actuators 106A-106F, e.g., 106F. As such, upon actuation/manipulation of actuator 106F, the resecting tool may be axially translated along elongate longitudinal slot 148 and the groove to resect, slice, separate, or otherwise cut tissue. In some arrangements, a common (e.g., same) actuator may simultaneously actuate both the actuating sled and the resecting tool. That is, in some arrangements, a single actuator, e.g., actuator 106E may be used to both eject fasteners from cartridge 128 into tissue and to sever tissue positioned along elongated longitudinal slot 148.

Notably, fastening head 134 may include a flexible joint 154 between a proximal end and a distal end of cartridge 128. That is, fastening head 134, including cartridge 128, may be flexible/bendable along a length thereof (e.g., along a longitudinal axis thereof). Joint 154 may include any one or more of a pivot, hinge, and/or ball and socket. In some arrangements, joint 154 may include a flexible feature so as to permit bending or deflecting one or more portions of fastening head 134/cartridge 128 relative to one or more other portions of fastening head 134/cartridge 128. Indeed, fastening head 134/cartridge 128 may be made of any appropriate material, e.g., a polymeric and/or a metallic material, and may be configured to permit or promote bending. That is, fastening head 134/cartridge 128 may include one or more portions of reduced thickness, cut-outs, grooves, notches, or the like arranged to permit bending. For example, as shown in FIGS. 3, 5A, and 5B, joint 154 of cartridge 128 may include one or more notches 156. Notches 156 may be generally v-shaped, as shown in FIG. 3, although the disclosure is not so limited. Indeed, notches 156 may have any appropriate shape configured to permit or promote bending. Additionally, while two notches 156 arranged on opposing sides of cartridge 128 are shown, any number, arrangement, orientation, or size may be used without departing from the scope of the present disclosure. Additionally, as shown in FIG. 3, one or more openings 158 or slots 160 may extend from a proximal end of cartridge 128 towards a distal end of cartridge 128. Such openings 158 or slots 160 may be arranged to receive one or more actuation lines coupled to one or more of actuators 106A-106F, as will be described in further detail below.

In use, a user may deliver endoscopic tissue fastening device 100 into the body of the subject, e.g., via a tortuous natural body lumen of the subject, while the endoscopic tissue fastening device 100 is arranged in the flexible configuration (FIGS. 1 and 2A). In the flexible configuration, as body 104 is articulated via manipulation of actuator 106A coupled to one or more articulation wires, tissue fastening assembly 116 may bend or deflect with body 104. That is, as body 104 bends and deflects during positioning within the body of the subject, so too does the tissue fastening assembly 116. Indeed, tissue fastening assembly 116 may bend and deflect with body 104 via one or both of flexible connection 122 and joint 154. As shown in FIGS. 1 and 2A, at least a portion of tissue fastening assembly 116 is supported (e.g., received by/within) support 146 secured to body 104. As such, articulation or deflection of body 104 will result in likewise movement of at least a portion of tissue fastening assembly 116. That is, while in the flexible configuration, tissue fastening assembly 116 may maintain generally parallel alignment between the central longitudinal axis L1 of second portion 1046 and the central longitudinal axis of L2 of tissue fastening assembly 116. In such a manner, endoscopic tissue fastening device 100 permits increased flexibility for precise positioning and delivery of endoscopic tissue fastening device 100 within the body of the subject.

Once endoscopic tissue fastening device 100 is positioned at or near a target location within the body of the subject, a user may transition the endoscopic tissue fastening device 100 to the stabilized configuration, as shown in FIG. 2E. As such, a user may activate/manipulate actuator 106B to move one or both of sheath 120 and fastening head 134 via actuation line 132. Such actuation may be performed in two stages. In a first stage, actuation of actuator 106B may move both sheath 120 and fastening head 134 axially (e.g., distally along central longitudinal axis L2 of tissue fastening assembly 116). Accordingly, in some arrangements, actuation line 132 may have an engagement feature (not shown) configured to interface with a corresponding engagement feature (not shown) of sheath 120 such that application of an axial force (e.g., in the distal direction) to actuation line 132 imparts a likewise axial force (e.g., in the distal direction) to sheath 120. Moreover, as sheath 120 is connected to fastening head 134 via flexible connection 122, application of an axial force to sheath 120 results in a likewise axial force being applied to fastening head 134. Said differently, in the first stage, actuation of actuator 106B may advance or extend both of sheath 120 and fastening head 134 until articulation joint 124 is located adjacent distal end face 108 or distal of distal end face 108. Next, in a second stage of actuation, the engagement feature of actuation line 132 may be disengaged from the engagement feature of sheath 120 such that actuation of actuator 106B may result in axial movement of actuation line 132 relative to sheath 120 and fastening head 134. In such a manner, continued application of the axial force to actuation line 132 may result in actuation line 132 moving along sheath 120 and through fastening head 134. For example, actuation line 132 may be axially advanced through the one or more openings 158 or slots 160 (FIG. 3) until actuation line 132 spans joint 154 (e.g., within fastening head 134). In some arrangements, however, actuation line 132 may be axially advanced alongside (e.g., outside of and next to) fastening head 134. Additionally or alternatively, a stabilizer 162 (FIGS. 4, 5A, 5B) may be coupled to actuation line 132 such that axial advancement of the actuation line 132 may result in stabilizer 162 spanning joint 154, as will be described in further detail below. Once actuation line 132 (or stabilizer 162) is so positioned, actuation line 132 (or stabilizer 162) may prevent bending or flexing of fastening head 134 along joint 154. Said differently, once actuation line 132 (or stabilizer 162) spans, covers, or extends through joint 154, fastening head 134 may be stabilized such that a distal portion 134B of fastening head 134 does not bend or deflect relative to proximal portion 134A of fastening head 134.

In some arrangements, the engagement feature of actuation line 132 may include a radially outward protrusion, ring, or the like that may selectively engage with a radially inward protrusion, ring, or the like of sheath 120. In some arrangements, one or both of the engagement features may be deflectable, bendable, or otherwise flexible such that during actuation (e.g., axial advancement), upon the application of an opposing axial force and/or stop, the engagement features may bend or flex so as to disengage from one another, thereby permitting movement of actuation line 132 relative to sheath 120 and fastening head 134. Such an opposing axial force or stop may be experienced when an abutment surface 166 (FIG. 2B) of flexible joint 122 interacts or abuts an edge of support 146. Alternatively, the engagement features may have a first radial orientation in which the engagement features are orientated to interfere with one another, and a second radial orientation in which the engagement features do not interfere with one another. That is, in the first radial orientation, the engagement feature of the actuation line 132 may be oriented so as to transmit an axial force imparted on the actuation line 132 to the engagement feature of sheath 120, and in the second radial orientation, the engagement feature of the actuation line 132 may be oriented so such that an axial force imparted on the actuation line 132 is not imparted to the engagement feature of sheath 120. In such cases, actuation line 132 may be rotated so as to move between the first radial orientation and the second radial orientation, and when the abutment surface 166 of flexible joint 122 interacts or abuts with an edge of support 146, the user may receive tactile feedback in the form of resistance at which point, the user may rotate the actuation line 132 relative to the sheath 120 to transition to the second radial orientation, thereby permitting actuation line 132 (and/or stabilizer 162) to continue advancing until joint 154 has been stabilized.

As shown in FIG. 2C, optionally, once stabilized, the user may articulate fastening head 134 at articulation joint 124 to direct fastening head 134 in any appropriate position. For example, as noted above, upon actuation of actuator 106C, fastening head 134 may move toward the central longitudinal axis L1 of second portion 1046 so as to be arranged in front of distal end face 108, and/or may be moved away from central longitudinal axis L1 of second portion 104B to so as to extend away from distal end face 108. In arrangements in which actuation line 132 spans across articulation joint 124, it is understood that actuation line 132 may include a portion configured to permit articulation along articulation joint 124. For example, the portion of actuation line 132 spanning articulation joint 124 may be relatively more flexible than a remainder of actuation line 132. Indeed, the portion of actuation line 132 spanning articulation joint 124 may have one or more portions of reduced cross-sectional size (e.g., may be thinned). In such a manner, actuation line 132 provides sufficient columnar support so as to extend through (or alongside) articulation joint 124 and toward fastening head 134 while still permitting articulation along articulation joint 124.

Next, as shown in FIG. 2D, anvil 130 may be moved toward or away from cartridge housing 126 and cartridge 128 via actuation actuator 106D. That is, upon actuation/manipulation of actuator 106D, anvil 130 may move toward the open configuration to form a tissue receiving space between anvil 130 and cartridge housing 126/cartridge 128, and after receiving tissue therebetween, may be closed so as to pinch tissue T (FIG. 2E) between anvil 130 and cartridge housing 126/cartridge 128 in the fastening configuration. Once so arranged, actuation or manipulation of actuator 106E may eject or deploy fasteners into tissue T. Additionally, upon actuation/manipulation of actuator 106F, the resecting tool (not shown) may be axially translated along elongate longitudinal slot 148 and the groove to resect, slice, separate, or otherwise cut tissue. As noted above, a single actuator, e.g., actuator 106E may be used to both eject fasteners from cartridge 128 into tissue and to sever tissue positioned along elongated longitudinal slot 148.

Figure 4:
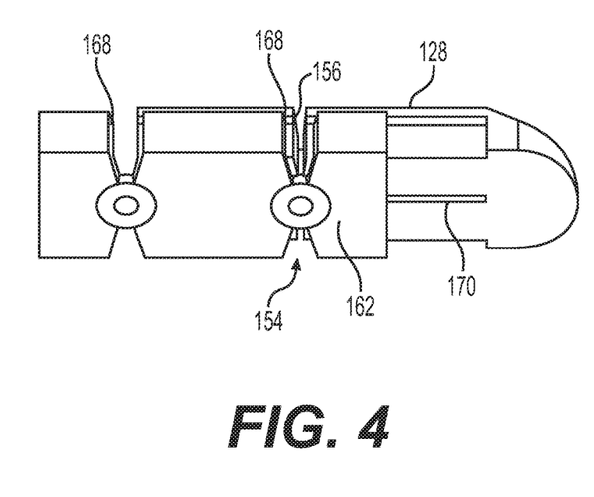
FIG. 4 is a perspective view of a stabilizer coupled to the staple cartridge of FIG. 3, according to aspects of this disclosure.

In arrangements in which stabilizer 162 is used, as shown in FIGS. 4, 5A, and 5B, stabilizer 162 may be axially advanced until stabilizer 162 spans joint 154. As such, stabilizer 162 may prevent bending or flexing of fastening head 134 along joint 154. For example, joint 154 may include notches 156, as discussed above. Likewise, stabilizer 162 may include one or more cut-outs, spaces, or notches 168. When notches 156 longitudinally align with notches 168, as shown in FIG. 5A, cartridge 128 (or fastening head 134) may be flexible or bendable. However, when notches 156 do not longitudinally align with notches 168 (e.g., when a solid, rigid, or otherwise un-notched portion of stabilizer 162 spans notches 156) as shown in FIG. 5B, cartridge 128 (or fastening head 134) may be prevented from flexing or bending. As such, cartridge 128 (or fastening head 134) may be considered stabilized. Additionally, as shown in FIG. 4, cartridge 128 and/or cartridge housing 126 may include a guide slot, groove, or channel 170 configured to receive a protrusion or post (not shown) of stabilizer 162 so as to maintain alignment between stabilizer 162 and cartridge 128 and/or cartridge housing 126 during advancement and retraction of stabilizer 162. In further arrangements, it is understood that cartridge 128 and/or cartridge housing 126 may include the post while stabilizer 162 may include the channel 170, without departing from the scope of the present disclosure.

Figure 6:
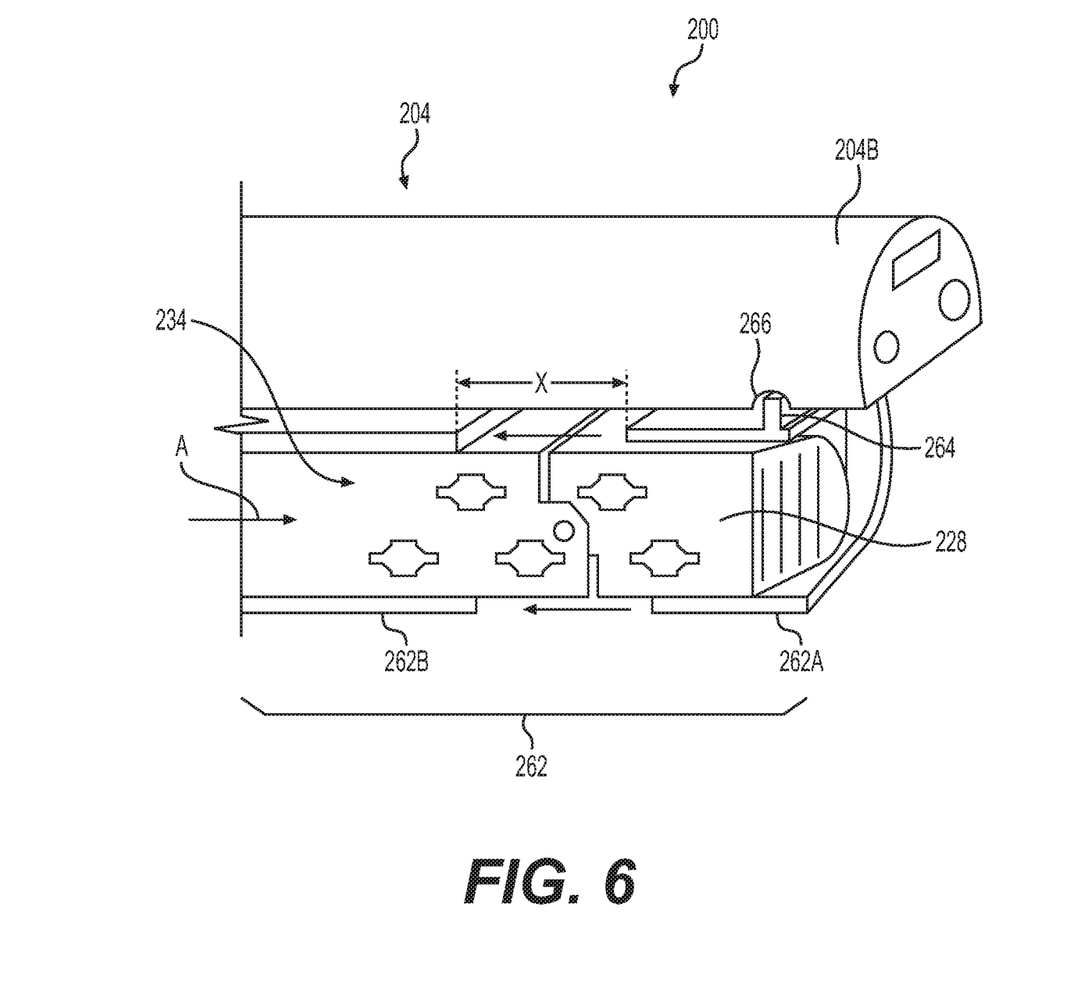
FIG. 6 is a top-view of an exemplary stabilization system of an endoscopic tissue fastening device, according to aspects of the present disclosure.

FIG. 6 is a top-view of an exemplary stabilizer of an endoscopic stapling device 200. Endoscopic stapling device 200 is similar to endoscopic tissue fastening device 100, and therefore, similar components will be referred to herein with similar reference numbers with the addition of 100. For example, as shown in FIG. 6, support 146 and stabilizer 162 may be replaced with stabilization system 262. Stabilization system 262 may include a first portion 262A and a second portion 262B. First portion 262A may be arranged distally of second portion 262B. For example, first portion 262A may be spaced a distance of X apart from second portion 262B. Additionally, first portion 262A may be selectively coupled to second portion 204B of body 204. For example, first portion 262A may include a connection feature 264 configured to cooperate within a connection recess 266 of second portion 204B of body 204. As shown in FIG. 6, connection feature 264 may include a protrusion, post, extension, or the like extending radially outwardly of first portion 262A, while connection recess 266 may be an indent, channel, groove, or notch extending radially into second portion 204B of body 204. First portion 262A of stabilizer system 262 may be selectively coupled to second portion 204B of body 204 via interaction between connection feature 264 and connection recess 266. When so coupled and an axial force in the direction A is applied to fastening head 234/cartridge 228, resistance between connection feature 264 and connection recess 266 may permit movement of fastening head 234/cartridge 228 relative to first portion 262A. In contrast, second portion 262B of stabilizer system 262 may be secured in any appropriate manner to fastening head 234/cartridge 228 for movement therewith. Accordingly, when an axial force in the direction A is applied to fastening head 234/cartridge 228, second portion 262B of stabilizer system 262 may likewise be moved in the direction A.

When advanced in the direction A, fastening head 234/cartridge 228, along with second portion 262B of stabilizer system 262, may be advanced toward first portion 262A, thereby reducing the distance X between first portion 262A and second portion 262B. However, when the distance X is equal to a value of zero (e.g., when there is no space between first portion 262A and second portion 262B), continued application of a force in the direction A will cause likewise force on first portion 262A. That is, a surface (e.g., distal end face) of second portion 262B may abut or contact a proximal end face of first portion 262A, and application of a force in the direction A may result in first portion 262A being pushed or advanced in the direction A. If the force in the direction A is sufficient, resistance between connection feature 264 and connection recess 266 may be overcome. That is, connection feature 264 may deflect or bend away from connection recess 266, or otherwise may be removed from connection recess 254. As such, first portion 262A may no longer be coupled to second portion 204B of body 204, and instead, may move with fastening head 234/cartridge 228, along with second portion 262B of stabilizer system 262. However, when the first and second portions 262A, 262B of stabilizer system contact/abut one another, stabilizer system 262 will be positioned so as to span (e.g., cover) a joint 254 along fastening head 234/cartridge 228. In such a manner, stabilization system 262 may stabilize fastening head 234/cartridge 228.

Figure 7:
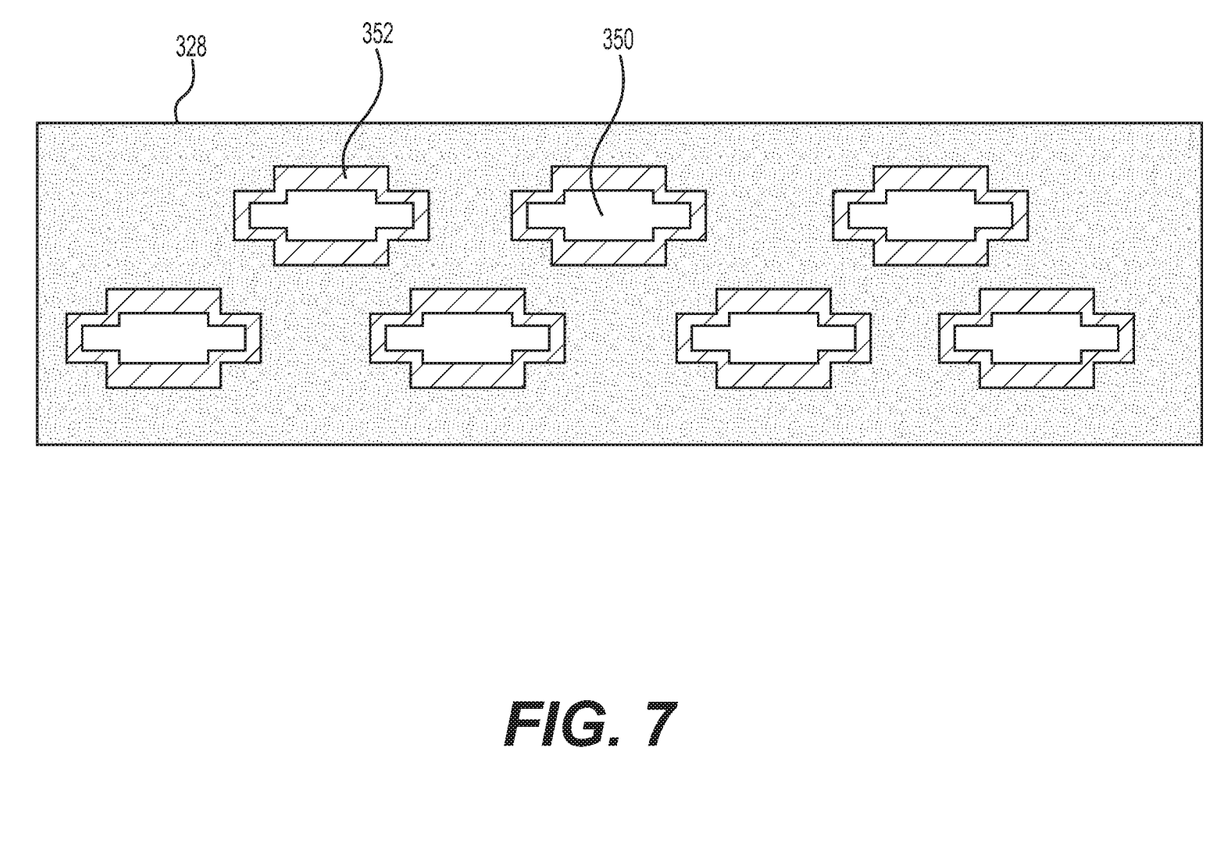
FIG. 7 is a top-view of an exemplary flexible stapler cartridge, according to aspects of the present disclosure.

FIG. 7 is a top-view of an exemplary flexible staple cartridge 328, according to aspects of the present disclosure. Staple cartridge 328 may be comprised of any appropriate elastomeric material, polymer, or otherwise flexible material so as to permit staple cartridge 328 to flex laterally during insertion into, or positioning within, the body of the subject. Additionally, staple cartridge 328 may include liners 352 lining each of the one or more slots 350 of staple cartridge 328. Liners 352 may be made of a relatively rigid material so as to maintain a shape of the one or more slots 350, and house/protect one or more staples and/or firing piston located within the one or more slots 350. In other words, while the staple cartridge 328 itself may be flexible and/or bendable, the liners 352 may be substantially noncompressible so as to support the one or more slots 350 during a stapling procedure.

Endoscopic tissue fastening device 100, 200 may be either disposable for single use, or may be equipped for multiple uses. For example, in some arrangements, endoscopic tissue fastening device 100, 200 may be a sterile single-use device, while in other arrangements endoscopic tissue fastening device 100, 200 may be reusable.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. An endoscopic tissue fastening device, comprising:
a shaft that terminates in a distal end face of the shaft;

a tissue fastening assembly, having a fastening head with a first arm and a second arm rotatably coupled to the first arm, wherein each of the first arm and the second arm includes a respective proximal end and a respective distal end, and wherein the first arm includes a staple cartridge; and a stabilizing means movably coupled to the staple cartridge of the tissue fastening assembly;

wherein, in a first, flexible configuration of the tissue fastening assembly, the stabilizing means permits bending of the staple cartridge at a joint of the staple cartridge between the proximal end and the distal end of the first arm, and wherein, in a second, stabilized configuration of the tissue fastening assembly, the stabilizing means spans the joint of the staple cartridge so as to prevent bending of the staple cartridge at the joint.

2. The endoscopic tissue fastening device of claim 1, wherein the shaft defines a lumen, and wherein at least a portion of the tissue fastening assembly is received within the lumen.

3. The endoscopic tissue fastening device of claim 1, wherein the shaft has a first portion and a second portion arranged alongside the first portion, wherein the second portion extends distally of the first portion, wherein a cross-sectional shape of the first portion is circular, and wherein a cross-sectional shape of the second portion is D-shaped.

4. The endoscopic tissue fastening device of claim 1, wherein, in the second, stabilized configuration, an entirety of the fastening head of the tissue fastening assembly is distal to the distal end face of shaft.

5. The endoscopic tissue fastening device of claim 1, wherein, in the second, stabilized configuration, the fastening head of the tissue fastening assembly is articulatable along an articulation joint proximal of the fastening head, such that a central longitudinal axis of the tissue fastening assembly is movable towards or away from the central longitudinal axis of the shaft.

6. The endoscopic tissue fastening device of claim 1, further including:

a support positioned along the shaft, wherein in the first, flexible configuration, a distal end of the tissue fastening assembly is received within the support.

7. The endoscopic tissue fastening device of claim 6, wherein at least a portion of the tissue fastening assembly is axially moveable relative to the support.

8. The endoscopic tissue fastening device of claim 6, wherein, in the second, stabilized configuration, a flexible connection of the tissue fastening assembly is received within the support and is prevented from flexing by the support, wherein the flexible connection is proximal of the tissue fastening assembly.

9. The endoscopic tissue fastening device of claim 1, wherein the tissue fastening assembly includes a sheath coupled to an articulation joint via a flexible connection, wherein the flexible connection includes at least one notch therein, wherein the first arm includes a staple cartridge, and wherein an entirety of the staple cartridge is distal of the articulation joint.

10. The endoscopic tissue fastening device of claim 1, wherein the stabilizing means includes a first wall portion and a second wall portion, wherein a gap separates the first wall portion from the second wall portion.

11. The endoscopic tissue fastening device of claim 10, wherein, in the first, flexible configuration, the joint of the staple cartridge aligns with the gap of the stabilizing means.

12. The endoscopic tissue fastening device of claim 11, wherein, in the second, stabilized configuration, the joint of the staple cartridge aligns with at least one of the first wall portion or the second wall portion.

* * * * *